(12) United States Patent
Nakamura et al.

(10) Patent No.: US 12,390,375 B2
(45) Date of Patent: Aug. 19, 2025

(54) DISPOSABLE WEARABLE ARTICLE

(71) Applicant: DAIO PAPER CORPORATION, Ehime (JP)

(72) Inventors: Wataru Nakamura, Ehime (JP); Masashi Furukawa, Ehime (JP)

(73) Assignee: Daio Paper Corporation, Ehime (JP)

( * ) Notice: Subject to any disclaimer, the term of this patent is extended or adjusted under 35 U.S.C. 154(b) by 443 days.

(21) Appl. No.: 17/800,765

(22) PCT Filed: Mar. 16, 2021

(86) PCT No.: PCT/JP2021/010574
§ 371 (c)(1),
(2) Date: Aug. 18, 2022

(87) PCT Pub. No.: WO2021/193228
PCT Pub. Date: Sep. 30, 2021

(65) Prior Publication Data
US 2023/0119436 A1    Apr. 20, 2023

(30) Foreign Application Priority Data
Mar. 25, 2020    (JP) .................................. 2020-054788

(51) Int. Cl.
*A61F 13/15*    (2006.01)
*A61F 13/511*    (2006.01)

(52) U.S. Cl.
CPC ............................... *A61F 13/51113* (2013.01)

(58) Field of Classification Search
CPC .................. A61F 13/51113; A61F 2013/51117
USPC .................................................. 604/359, 360
See application file for complete search history.

(56) References Cited

U.S. PATENT DOCUMENTS

| | | | |
|---|---|---|---|
| 5,176,672 A * | 1/1993 | Bruemmer | A61F 13/495 |
| | | | 604/385.19 |
| 5,192,606 A * | 3/1993 | Proxmire | A61F 13/513 |
| | | | 604/378 |
| 6,533,765 B1 | 3/2003 | Blaney et al. | |
| (Continued) | | | |

FOREIGN PATENT DOCUMENTS

| | | |
|---|---|---|
| EP | 0692263 | 1/1996 |
| EP | 0967949 | 1/2000 |
| (Continued) | | |

OTHER PUBLICATIONS

International Search Report for PCT/JP2021/010574, dated Jun. 1, 2021.

*Primary Examiner* — Jacqueline F Stephens
(74) *Attorney, Agent, or Firm* — Andrus Intellectual Property Law, LLP

(57) ABSTRACT

A disposable wearable article including a top sheet having a skin-touching region that is brought into contact with skin of a wearer, wherein the top sheet is made from discontinuous fiber nonwoven fabric having a fineness of 1 to 3 dtex, a basis weight of 10 to 30 g/m², and a thickness of 0.4 to 1.4 mm, wherein the skin-touching region has a lotion-bearing zone which bears a water-containing hydrophilic lotion, the lotion-bearing zone having a MD dimension of 30 mm or larger and a CD dimension of 5 mm or larger, and wherein an average coefficient of friction MIU of the lotion-bearing zone is 0.2 to 0.4.

3 Claims, 12 Drawing Sheets

(56) References Cited

U.S. PATENT DOCUMENTS

| | | | | |
|---|---|---|---|---|
| 6,756,520 | B1 * | 6/2004 | Krzysik | .................. A61L 15/34 604/360 |
| 2008/0287896 | A1 | 11/2008 | Vega et al. | |
| 2020/0060882 | A1 | 2/2020 | Cecchetto | |

FOREIGN PATENT DOCUMENTS

| | | |
|---|---|---|
| JP | H8-052175 | 2/1996 |
| JP | 2002-509457 | 3/2002 |
| JP | 2003-526468 | 9/2003 |
| JP | 2010-526630 | 8/2010 |
| JP | 2013-066598 | 4/2013 |
| JP | 2017-184962 | 10/2017 |
| JP | 2018-513749 | 5/2018 |
| JP | 2019-170534 | 10/2019 |
| WO | 2020/041534 | 2/2020 |

* cited by examiner

[FIG.1]
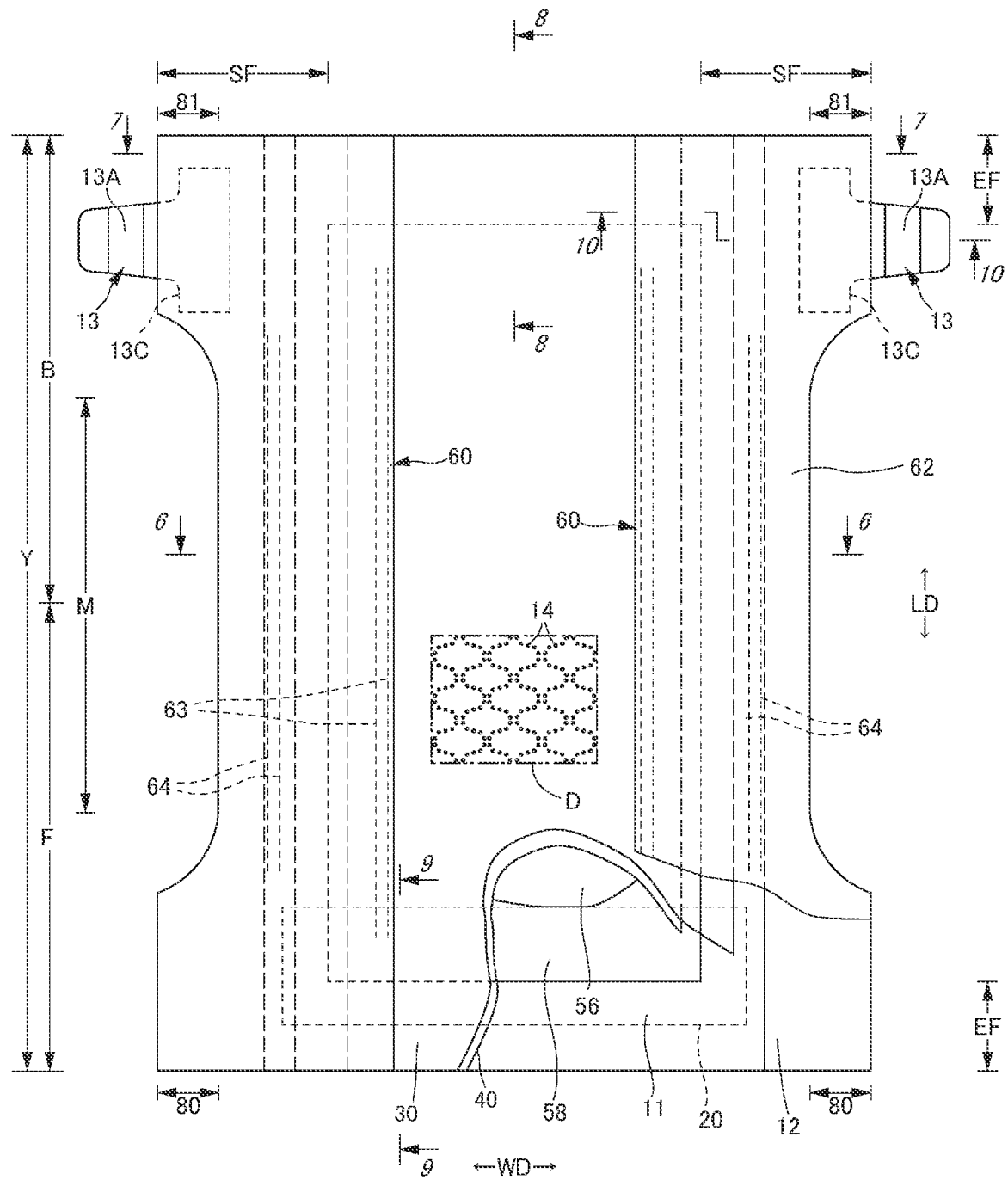

[FIG.2]
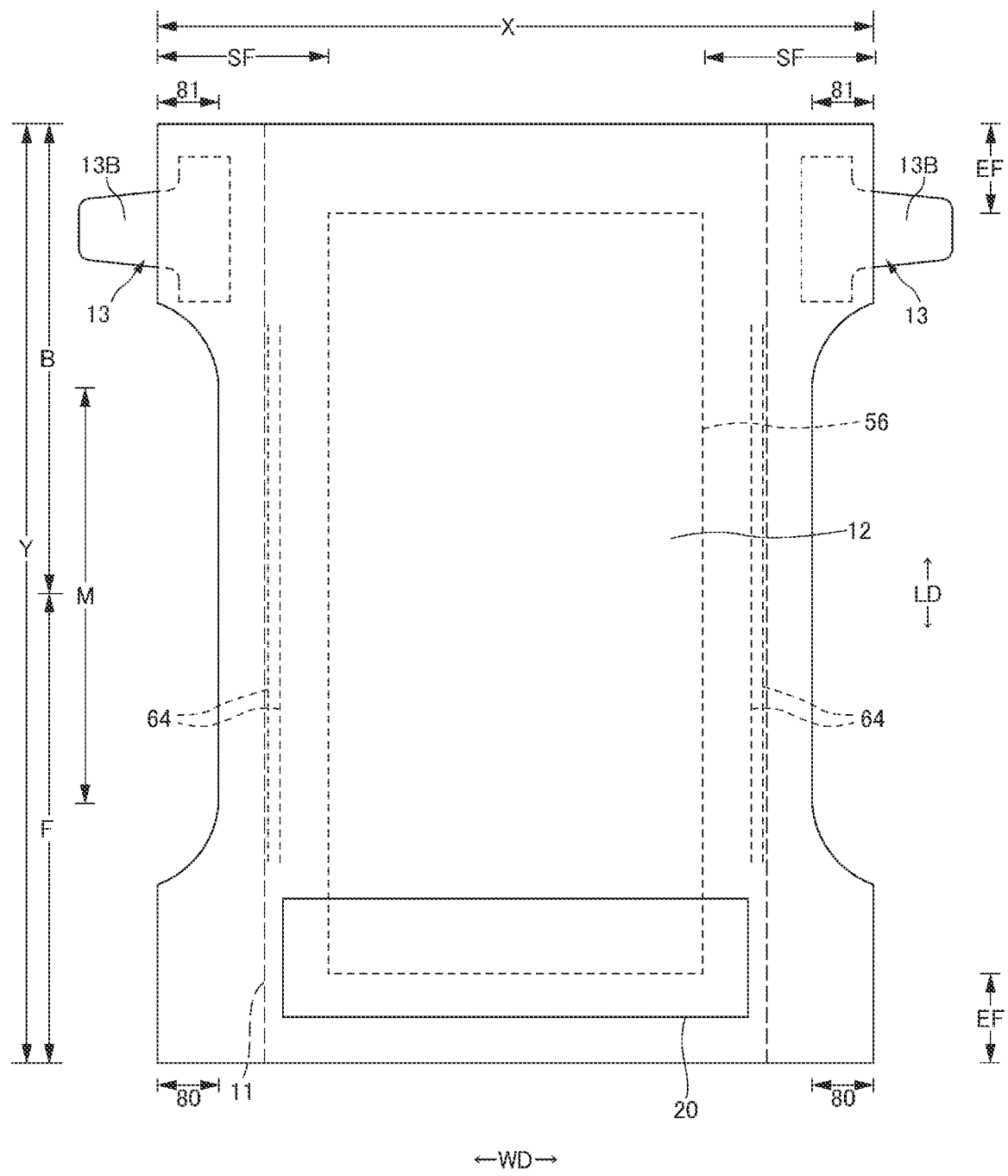

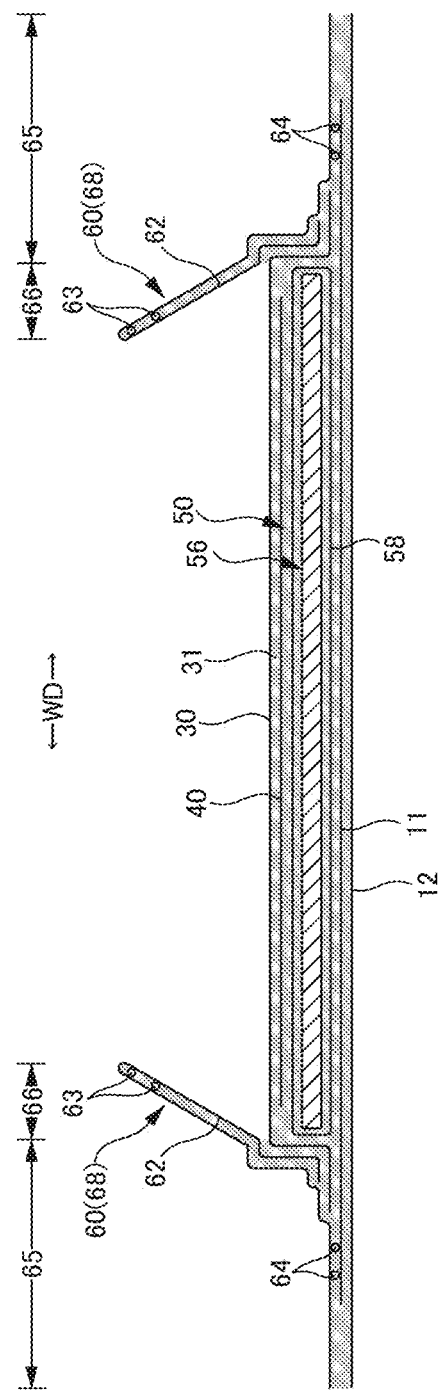
[FIG.3]

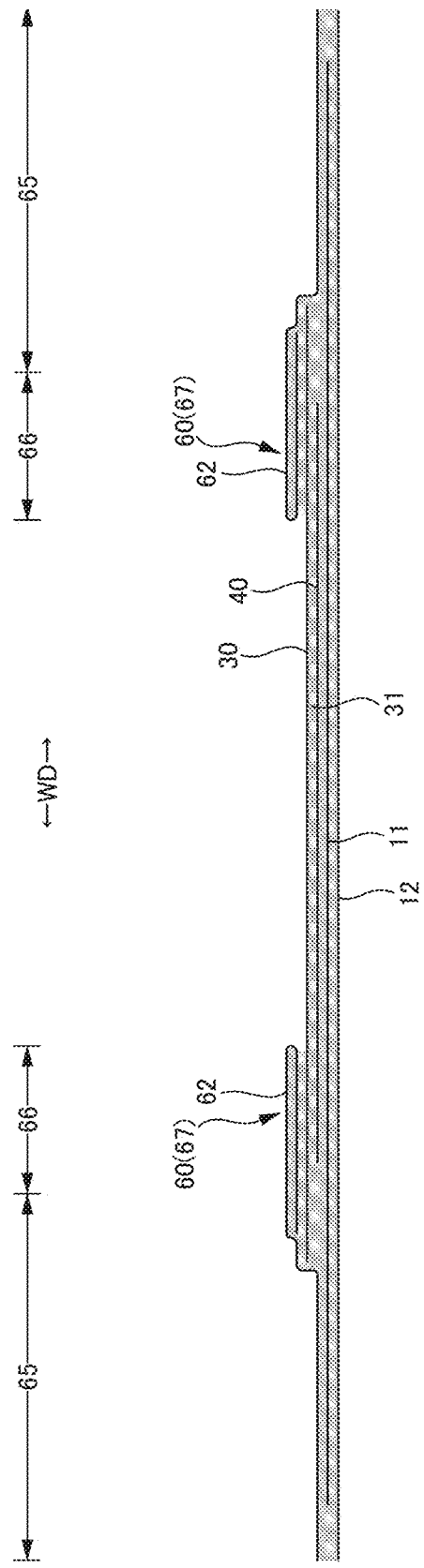
[FIG.4]

[FIG.5]
(a)
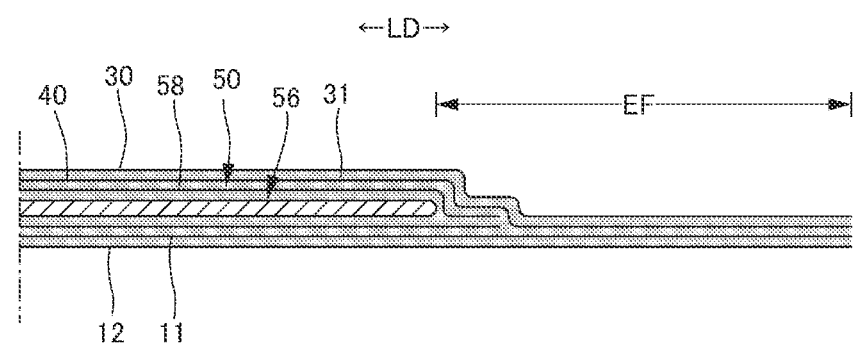
(b)
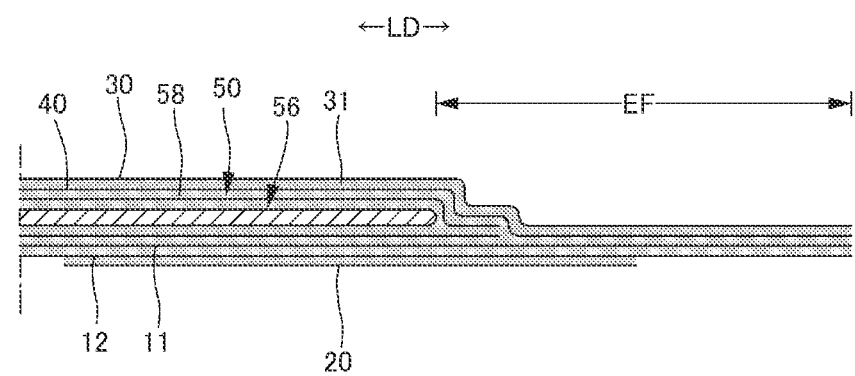
(c)
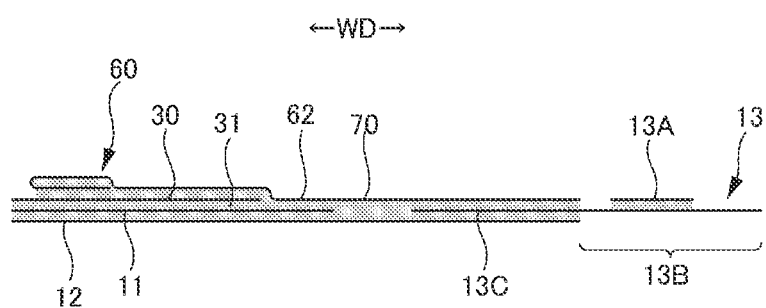

[FIG.6]
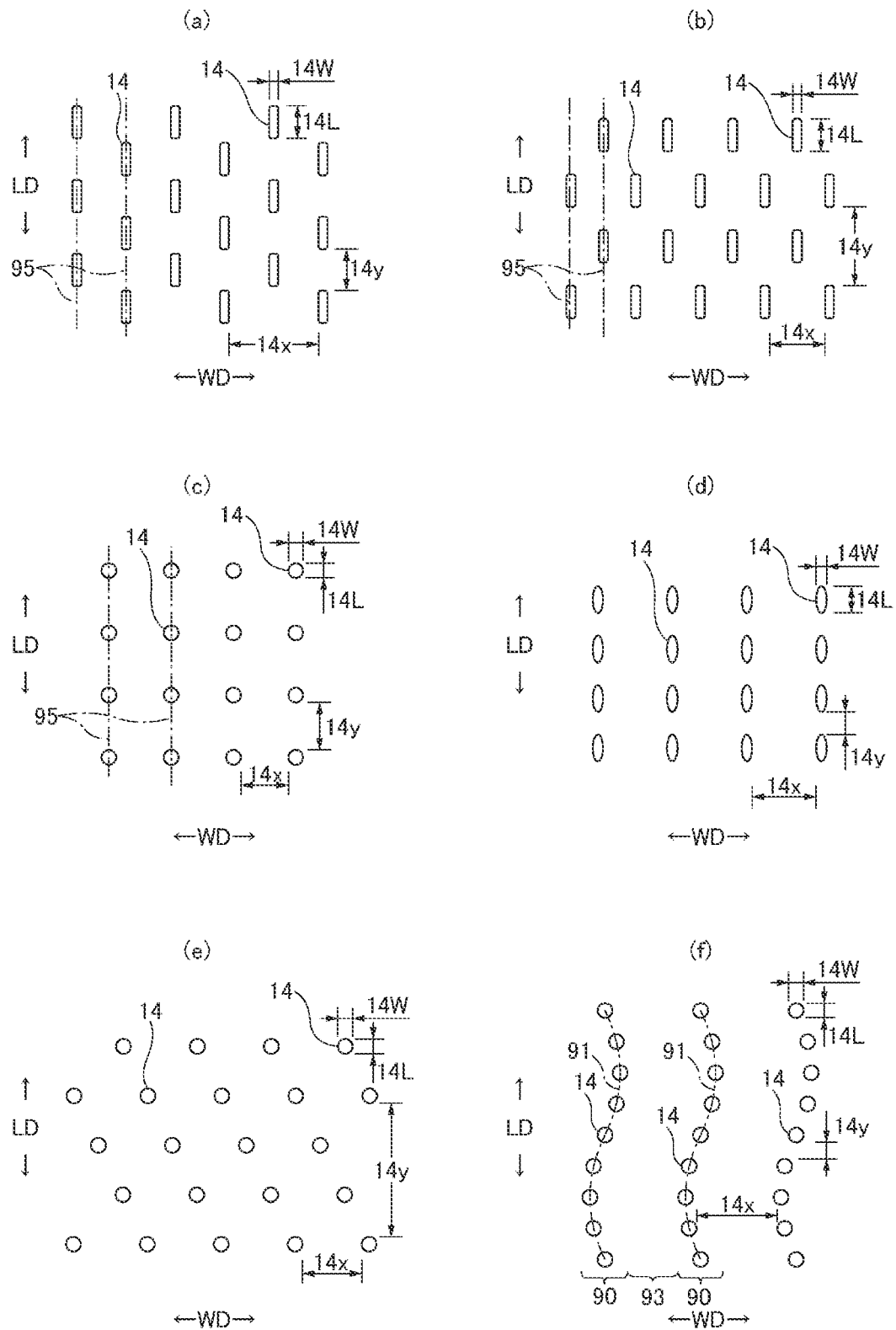

[FIG.7]
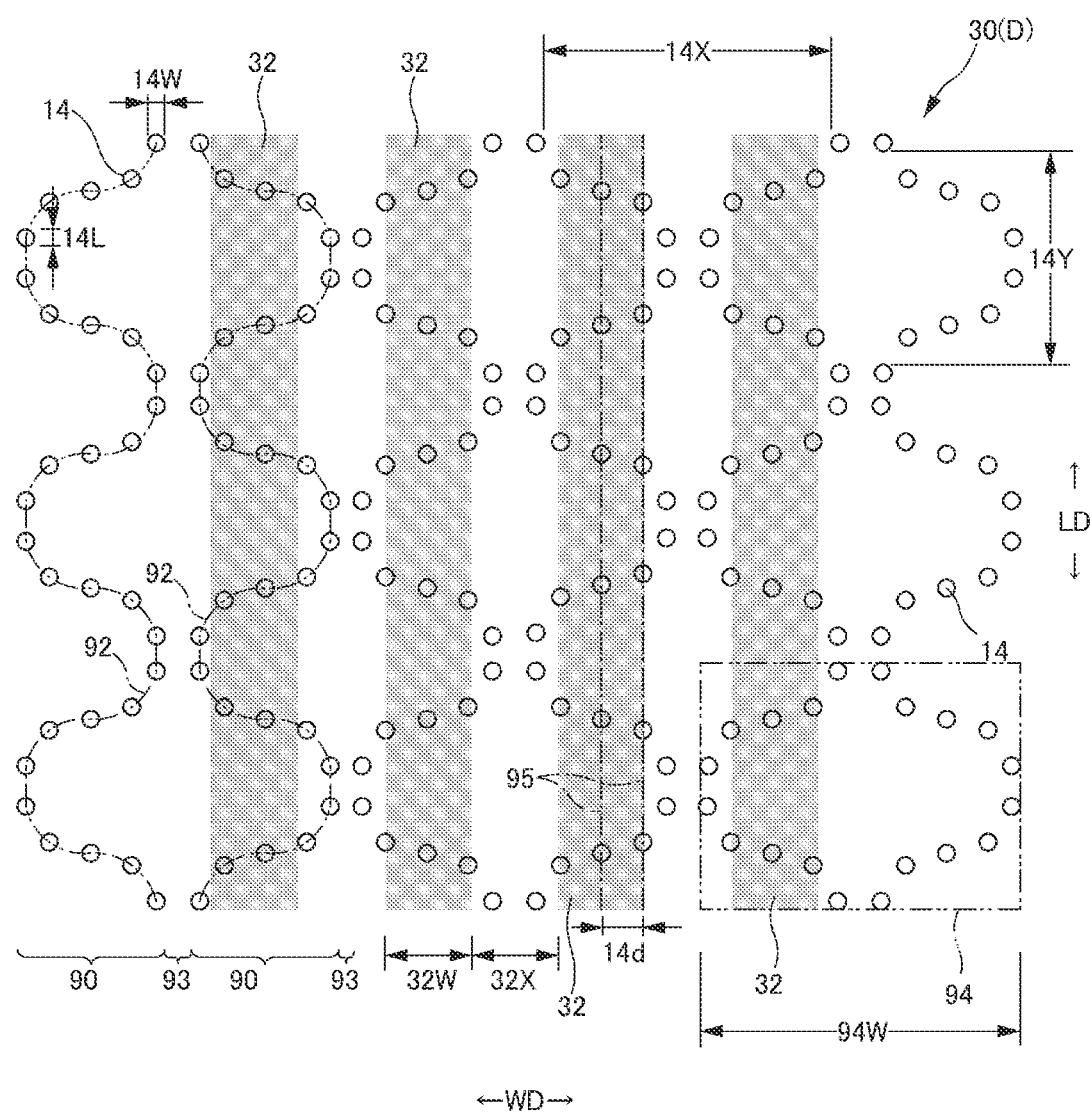

[FIG.8]
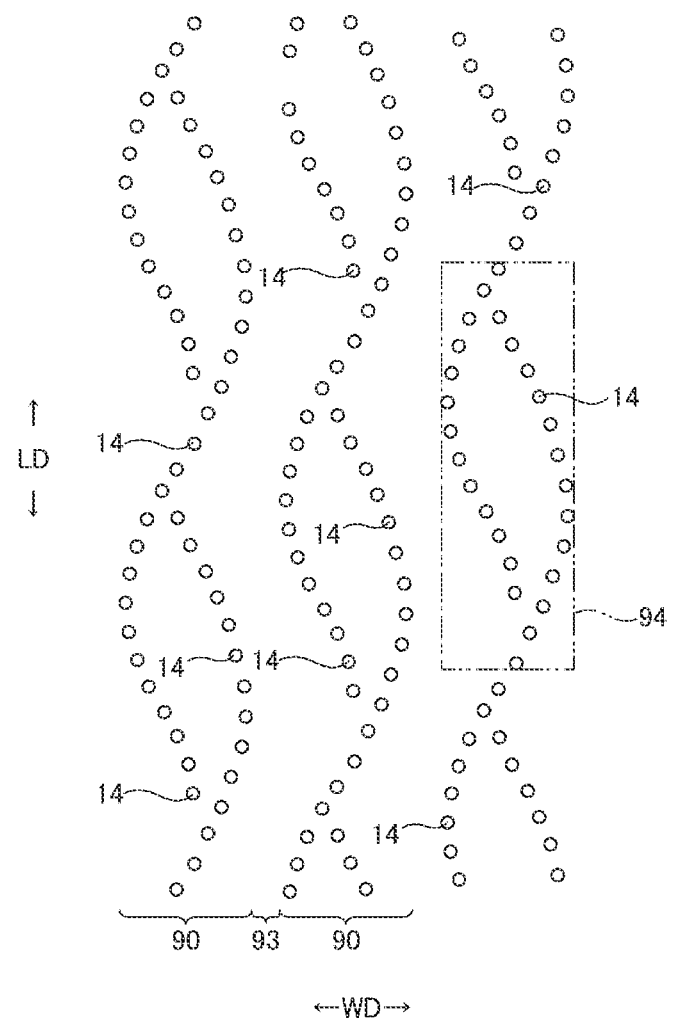

[FIG.9]
(a)
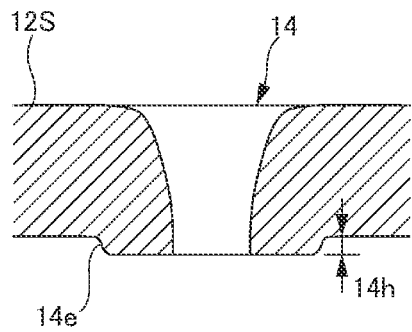
(b)
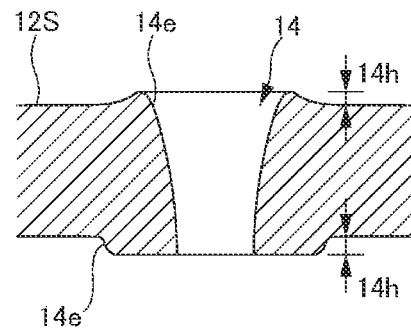
(c)
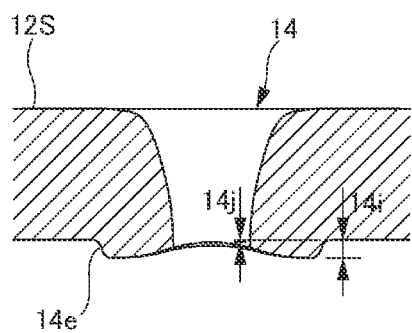
(d)
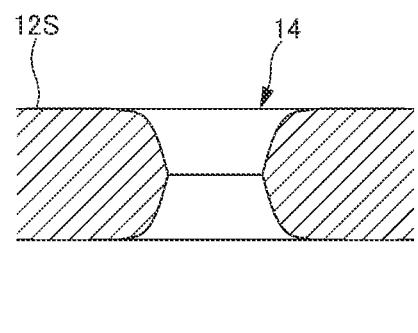

[FIG.10]
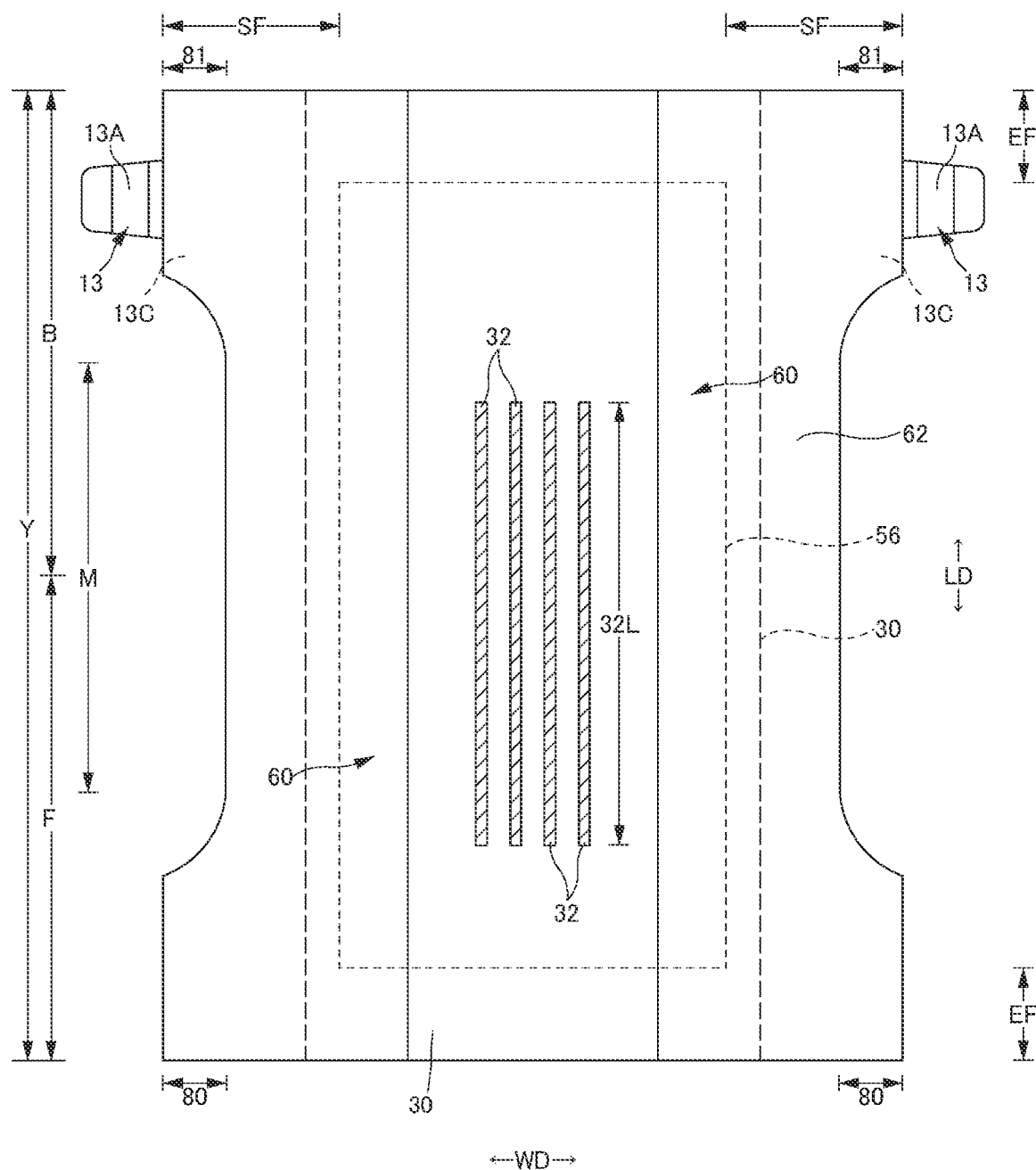

[FIG.11]
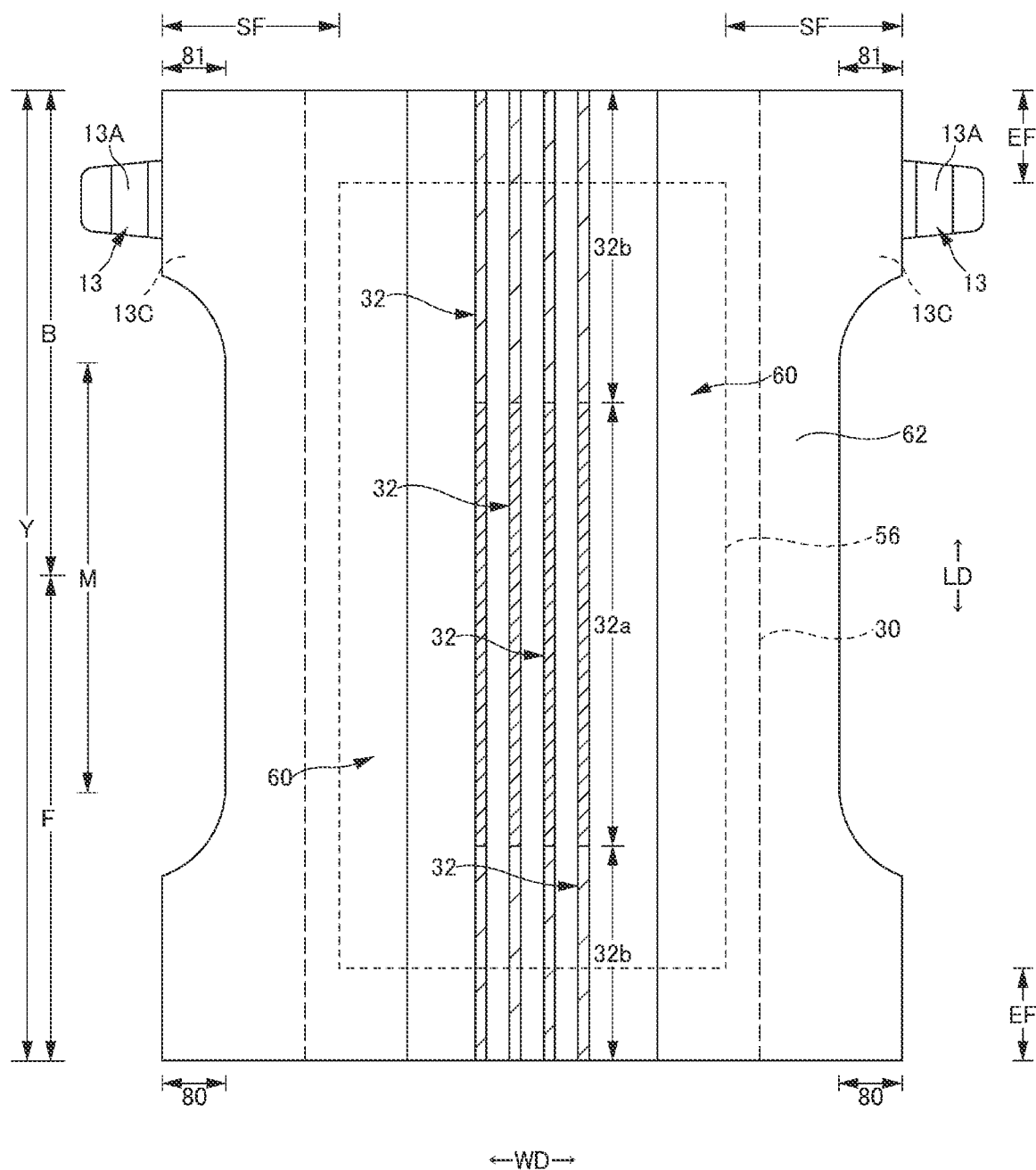

[FIG.12]
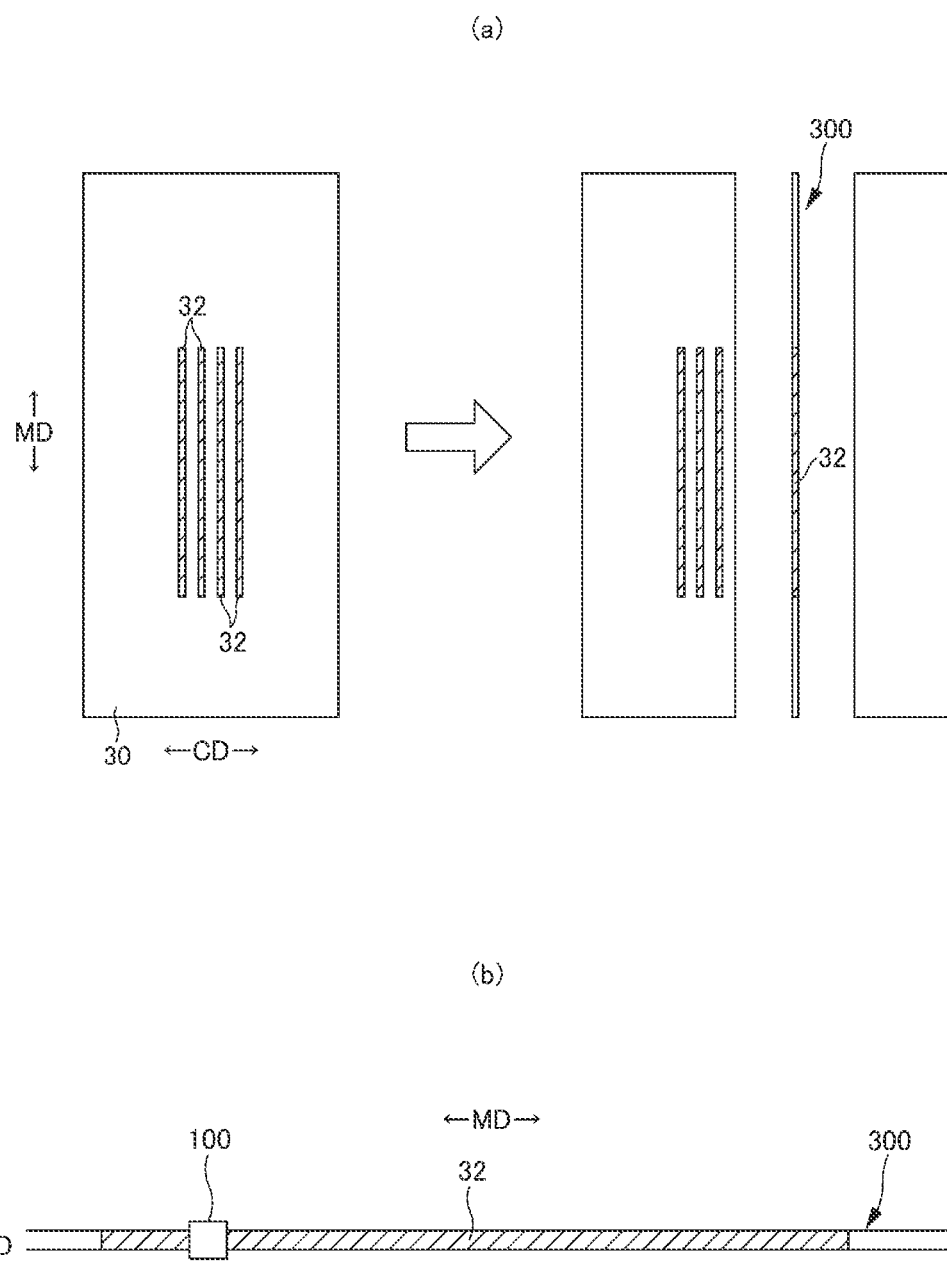

DISPOSABLE WEARABLE ARTICLE

CROSS-REFERENCE TO RELATED APPLICATIONS

This application is the U.S. national stage application of International Application PCT/JP2021/010574, filed Mar. 16, 2021, which international application was published on Sep. 30, 2021, as International Publication WO 2021/193228 in the Japanese language. The International Application claims priority of Japanese Patent Application No. 2020-054788, filed Mar. 25, 2020. The international application and Japanese application are both incorporated herein by reference, in entirety.

TECHNICAL FIELD

The present invention relates to disposable wearable articles, including disposable diapers and sanitary napkins.

BACKGROUND ART

Disposable wearable articles, in particular, disposable diapers, often pose skin problems, particularly, skin rash of wearers. Such problems may result from physical irritation (friction or coarseness) to the skin or skin dryness of wearers.

There is proposed to cause a wax-like substance having a higher softening point than the human body temperature to be contained in a nonwoven top sheet for reducing friction between the skin of a wearer and the top sheet (Patent Literature 1).

For the purpose of reducing friction, there is also known to apply a hydrophilic lotion to a nonwoven top sheet (Patent Literature 2). This hydrophilic lotion is preferred for its capability of avoiding hardness of the wax-like substance or lowering of liquid-permeability. In particular, a water-containing hydrophilic lotion is preferred for keeping the skin from drying.

However, application of a water-containing hydrophilic lotion to a top sheet made from discontinuous fiber nonwoven fabric resulted in a problem of less increase in the effect of reducing friction than expected.

PRIOR ART LITERATURE

Patent Literature

Patent Literature 1: JP H08-52175 A
Patent Literature 2: JP 2010-526630 A
Patent Literature 3: JP 2002-509457 A
Patent Literature 4: JP 2019-170534 A

SUMMARY OF THE INVENTION

Problems to be Solved by the Invention

It is therefore a primary object of the present invention to improve the effect of reducing friction on a top sheet, or the like.

Means for Solving the Problem

The present inventors, in studying nonwoven top sheets bearing water-containing hydrophilic lotions, have obtained the following knowledge. It is conceivable that, when a water-containing hydrophilic lotion is applied to a top sheet made from discontinuous fiber nonwoven fabric, the hydrophilic lotion is prone to transfer to the absorber body side after the production, and is harder to be retained in the top sheet than expected, which results in a lower friction-reducing effect than expected. The disposable wearable articles to be discussed below are based on such knowledge.

<First Aspect>

A disposable wearable article including a top sheet having a skin-touching region that is brought into contact with skin of a wearer,
  wherein the top sheet is made from discontinuous fiber nonwoven fabric having a fineness of 1 to 3 dtex, a basis weight of 10 to 30 g/m$^2$, and a thickness of 0.4 to 1.4 mm,
  wherein the skin-touching region has a lotion-bearing zone which bears a water-containing hydrophilic lotion, the lotion-bearing zone having a machine direction dimension of 30 mm or larger and a cross direction dimension of 5 mm or larger, and
  wherein an average coefficient of friction MIU of the lotion-bearing zone is 0.2 to 0.4.

(Effect)

According to the present disposable wearable article, in the combination of a hydrophilic lotion and a discontinuous fiber nonwoven top sheet, nonwoven fabric of fine fibers is employed. With such discontinuous fiber nonwoven fabric, fineness of the fibers contributes to reduction of surface friction, which, in cooperation with the friction-reducing effect of the hydrophilic lotion, improves the overall friction-reducing effect. In addition, the fineness of the fibers also improves the hydrophilic lotion-retainability, which further improves the friction-reducing effect.

Note that, with too small dimensions of the lotion-bearing zone, the friction-reducing effect is localized, which provides little significance in protection of the skin of a wearer.

<Second Aspect>

The disposable wearable article according to the first aspect, wherein the lotion-bearing zone has a surface moisture percentage of 3 to 10%.

(Effect)

With the surface moisture percentage of the lotion-bearing zone falling within the above-mentioned range, the skin of a wearer may be moistened moderately so as to be kept from drying.

<Third Aspect>

The disposable wearable article according to the second aspect,
  wherein the hydrophilic lotion contains 70 to 90 wt % glycerin and 10 to 30 wt % water, and
  wherein a content of the hydrophilic lotion per unit area of the lotion-bearing zone is 5 to 15 g/m$^2$.

(Effect)

The composition of the hydrophilic lotion and the content of the lotion in the lotion-bearing zone may suitably be decided, and preferably within the ranges of the present aspect.

<Fourth Aspect>

The disposable wearable article according to any one of the first to third aspects,
  wherein the discontinuous fiber nonwoven fabric is formed of nonwoven fabric of hydrophilized fibers in which hydrophobic resin fibers have been coated with a hydrophilizer.

(Effect)

The discontinuous fiber nonwoven fabric is preferably formed of hydrophobic resin fibers for their low cost, which as they are have poor retainability of the water-containing hydrophilic lotion. Accordingly, in the present aspect, it is preferred to use discontinuous fiber nonwoven fabric formed of hydrophilized fibers employing a hydrophilizer to improve the hydrophilic lotion-retainability of the discontinuous fiber nonwoven fabric.

<Fifth Aspect>

The disposable wearable article according to any one of the first to fourth aspects, wherein the hydrophilic lotion has a viscosity at a temperature of 20° C. of 150 to 400 mPa·s.

(Effect)

The discontinuous fiber nonwoven fabric is preferably formed of hydrophobic resin fibers for their low cost, which as they are have poor retainability of the water-containing hydrophilic lotion. Accordingly, it is preferred to set the viscosity of the hydrophilic lotion within the range of the present aspect to improve the hydrophilic lotion-retainability of the discontinuous fiber nonwoven fabric.

Effect of the Invention

The present invention provides advantages such as improvement in the effect of reducing friction on the top sheet.

BRIEF DESCRIPTION OF THE DRAWINGS

FIG. 1 is a plan view of a tape-type disposable diaper in its spread state, illustrating the interior surface thereof.

FIG. 2 is a plan view of the tape-type disposable diaper in its spread state, illustrating the exterior surface thereof.

FIG. 3 is a cross-sectional view taken along lines 6-6 in FIG. 1.

FIG. 4 is a cross-sectional view taken along lines 7-7 in FIG. 1.

FIG. 5(a) is a sectional view taken along lines 8-8 in FIG. 1, FIG. 5(b) is a sectional view taken along lines 9-9 in FIG. 1, and FIG. 5(c) is a sectional view taken along lines 10-10 in FIG. 1.

FIG. 6 shows plan views of various examples of the aperture pattern in the perforated nonwoven fabric.

FIG. 7 is a plan view illustrating an example of the aperture pattern (Moroccan pattern) in the perforated nonwoven fabric.

FIG. 8 is a plan view illustrating an example of the aperture pattern (chain pattern) in the perforated nonwoven fabric.

FIG. 9 shows sectional views of the apertures in the perforated nonwoven fabric.

FIG. 10 is a plan view of a tape-type disposable diaper in its spread state, illustrating the interior surface thereof.

FIG. 11 is a plan view of a tape-type disposable diaper in its spread state, illustrating the interior surface thereof.

FIG. 12 shows plan views for explaining a specimen.

EMBODIMENTS FOR CARRYING OUT THE INVENTION

FIGS. 1 to 5 show a tape-type disposable diaper as an example of a disposable wearable article. In the figures, reference sign X refers to the overall width of the diaper exclusive of the connecting tapes, whereas reference sign Y refers to the overall length of the diaper. In the sectional views, dotted pattern regions represent an adhesive as joining means for joining various components. A hot melt adhesive may be applied using a known technique, such as slot application, bead application in continuous lines or dotted lines, spray application in spiral, Z, or wave shapes, or pattern coating (transfer of a hot melt adhesive by relief printing). In place of or in addition to these, fixing portions of elastic members may be fixed to adjacent members by application of a hot melt adhesive to the outer peripheral surface of the elastic members. Examples of the hot melt adhesive include, but not limited to, EVA-based, pressure-sensitive rubber-based (elastomer-based), polyolefin-based, and polyester/polyamide-based adhesives. The joining means for joining various components may alternatively be material melt-bonding, such as heat sealing or ultrasonic sealing.

As the nonwoven fabric in the description hereinbelow, commonly known nonwoven fabric may suitably be used depending on the parts or purposes. Examples of the constituent fibers of the nonwoven fabric include, but not limited to, synthetic fibers, such as polyolefin-based, e.g., polyethylene or polypropylene, polyester-based, or polyamide-based fibers (including not only single component fibers, but also composite fibers, such as of core/sheath type), as well as regenerated fibers, such as rayon or cupra, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, nonwoven fabric may generally be categorized into discontinuous fiber nonwoven fabric, continuous fiber nonwoven fabric, spunbonded nonwoven fabric, melt blown nonwoven fabric, spunlace nonwoven fabric, thermal bonded (air through) nonwoven fabric, needle-punched nonwoven fabric, point-bonded nonwoven fabric, composite nonwoven fabric (SSS nonwoven fabric having the same or similar nonwoven layers laid one on top of another, as well as SMS or SMMS nonwoven fabric having different nonwoven layers laid one on top of another, i.e., melt blown layer interposed between spunbonded layers), or the like, generally depending on the length of the fibers, method of forming the sheet, method of joining the fibers, or layered structure, and any of these nonwoven fabric may be used. The composite nonwoven fabric refers to those having all the layers integrally manufactured and subjected to fiber joining process all over the layers, and does not include those having a plurality of nonwoven fabric layers separately manufactured and bonded with joining means, such as hot melt adhesives.

The present tape-type disposable diaper has a ventral section F extending forward of the middle of the diaper in the front-back direction LD and a dorsal section B extending backward of the middle of the diaper in the front-back direction LD. The present tape-type disposable diaper is configured with a crotch section M extending from forward of the middle of the product to backward of the middle of the product in the front-back direction, front wings 80 extending on opposed sides in the right-left direction at a position spaced forward of the middle of the product in the front-back direction, and back wings 81 extending on opposed sides in the right-left direction at a position spaced backward of the middle of the product in the front-back direction. Further, the present tape-type disposable diaper includes an absorber body 56 internally disposed within a region including the crotch section, a liquid-pervious top sheet 30 covering the top side of the absorber body 56, a liquid-impervious sheet 11 covering the underside of the absorber body 56, and an exterior nonwoven sheet 12 covering the underside of the liquid-impervious sheet 11 to constitute the product exterior surface.

Materials and features of each part will now be explained in turn.

(Absorber Body)

The absorber body 56 absorbs and holds excreted fluid, and may be formed of an assembly of fibers. Such an assembly of fibers may be a stack of discontinuous fibers of fluff pulp, synthetic fibers, or the like, as well as an assembly of filaments obtained by opening, where necessary, tows (fiber bundles) of synthetic fibers, such as cellulose acetate. The basis weight of the fibers may be about 100 to 300 $g/m^2$ for a stack of fluff pulp or discontinuous fibers, and about 30 to 120 $g/m^2$ for an assembly of filaments. The fineness of the synthetic fibers, when used, is, for example, 1 to 16 dtex, preferably 1 to 10 dtex, more preferably 1 to 5 dtex.

The plan shape of the absorber body 56 may suitably be decided, and may be in a rectangular shape or a shape having a middle portion in the front-back direction LD narrowed so as to fit around each leg.

(Superabsorbent Polymer Particles)

The absorber body 56 may be caused partially or entirely to contain superabsorbent polymer particles. The superabsorbent polymer particles include not only "particles", but also "powders". Superabsorbent polymer particles used in this type of absorbent articles may be used as they are as the superabsorbent polymer particles here. The particle size of the superabsorbent polymer particles is not particularly limited and, for example, the particles may preferably have such a particle size that, when the particles are subjected to sieving (five-minute shaking) through a 500 μm standard sieve (JIS Z8801-1: 2006), followed by further sieving (five-minute shaking) through a 180 μm standard sieve (JIS Z8801-1: 2006) of the particles sieved through the previous sieve, the percentage of the particles remaining on the 500 μm standard sieve is 30 wt % or less and the percentage of the particles remaining on the 180 μm standard sieve is 60 wt % or more.

Any materials of the superabsorbent polymer particles may be used without particular limitation, and those having a water absorption of 40 g/g or more are preferred. The superabsorbent polymer particles may be starch-based, cellulose-based, or synthetic polymer-based, and starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption rate of 70 seconds or less, particularly 40 seconds or less, may preferably be used. With too slow a water absorption rate, the absorber body 56 is likely to undergo so-called back flow, wherein liquid supplied into the absorber body 56 returns out of the absorber body 56.

The superabsorbent polymer particles may preferably be those having a gel strength of 1000 Pa or higher. With such property, when the superabsorbent polymer particles are formed into a bulky absorber body 56, stickiness after liquid absorption may effectively be limited.

The basis weight of the superabsorbent polymer particles may suitably be decided depending on the absorption amount required in a use of the absorber body 56. Thus, it depends, but the basis weight may usually be 50 to 350 $g/m^2$.

(Packing Sheet)

For limiting escape of the superabsorbent polymer particles, or for improving maintenance of the shape of the absorber body 56, the absorber body 56 may be wrapped with a packing sheet 58 to produce an absorbent element 50, which is to be disposed inside. The packing sheet 58 may be tissues, in particular, crepe paper, nonwoven fabric, polyethylene-laminated nonwoven fabric, perforated sheet, or the like, provided that sheets through which the superabsorbent polymer particles will not escape are preferred. When nonwoven fabric is used in place of crepe paper, hydrophilic SMMS (spunbonded/melt-blown/melt-blown/spunbonded) nonwoven fabric is particularly preferred, which may be made of polypropylene, polyethylene/polypropylene, or the like. The basis weight is preferably 5 to 40 $g/m^2$, particularly 10 to 30 $g/m^2$.

One such packing sheet 58 may be used, as shown in FIG. 3, to wrap the entire absorber body 56, or a plurality of sheets, such as an upper sheet and a lower sheet, may be used to wrap the entire absorber body 56. Alternatively, the packing sheet 58 may be omitted.

(Top Sheet)

The top sheet 30 extends in the front-back direction from the front end to the back end of the product, and in the width direction WD laterally beyond the absorber body 56, but its shape may suitably be modified, for example, so that the width of the top sheet 30 is shorter than the entire width of the absorber body 56, in case, for example, the starting points of standup gather parts 60 to be discussed later are located on the center side of the side edges of the absorber body 56 in the width direction WD, or otherwise required.

The top sheet 30 has a skin-touching region that is brought into contact with the skin of a wearer, and is preferably made from nonwoven fabric in light of liquid permeability and texture. Various nonwoven fabric may be used as the top sheet 30 but, in view of cushioning property, flexibility, permeability of loose stool (watery or muddy stool), or the like factors, discontinuous fiber nonwoven fabric, such as air-through nonwoven fabric, is preferred rather than continuous fiber (long fiber) nonwoven fabric and, usually, discontinuous fiber nonwoven fabric generally having a fineness of 1 to 10 dtex, a basis weight of 10 to 30 g/m2, and a thickness of 0.4 to 1.4 mm, is preferred. The fiber length of the discontinuous fiber nonwoven fabric is not particularly limited, and is preferably about 0.5 to 1.0 mm.

The top sheet 30 is particularly preferably a perforated nonwoven fabric having an aperture arrayed region wherein apertures 14 each penetrating two sides of the fabric are arrayed in a particular pattern. The shape and size of each aperture 14, the pattern of the array, or the like, may suitably be decided. Note that, in FIG. 1, for ready conception of the figure, the apertures 14 are illustrated only in a part D of the top sheet 30, which, however, does not represent the aperture arrayed region.

The aperture arrayed region may be positioned only in the middle of the top sheet 30 in the front-back direction LD or only in the middle of the top sheet 30 in the width direction WD (the top sheet 30 may partially have a zone without any aperture 14). Alternatively, the aperture arrayed region may be provided all over the top sheet 30. That is, the aperture arrayed region may extend, as long as it is provided over the skin-touching region, to the other region (for example, the regions where the gathered sheets 62 are bonded on opposed sides in the width direction WD).

The plan shape of each aperture 14 (opening shape) may suitably be decided. Each aperture 14 may be in a slot shape as shown in FIGS. 6(*a*) and 6(*b*), perfect circular as shown in FIGS. 6(c), 6(e), and 6(f) as well as in FIGS. 7 and 8, elliptical as shown in FIG. 6(d), polygonal, such as triangular, rectangular, or rhombic, start shaped, cloud shaped, or any arbitrary shape. Though not shown, apertures 14 of different shapes may be present. The size of each aperture 14 is not particularly limited, and the dimension 14 L in the front-back direction (the maximum dimension) is preferably 0.5 to 2.0 mm, particularly 0.5 to 1.0 mm, and the dimension 14 W in the width direction (the maximum dimension) is preferably 0.5 to 2.0 mm, particularly 0.5 to 1.0 mm. When the shape of each aperture 14 is longer in the front-back direction (the overall dimension in one direction is longer than the overall dimension in the direction orthogonal thereto), such as a slot, elliptical, rectangular, or rhombic shape, the front-back dimension is preferably 1.2 to 2.5 times the dimension in the width direction orthogonal thereto. Further, when the shape of each aperture 14 is longer in one direction, the longitudinal direction of the apertures 14 is preferably aligned to the machine direction (MD) of the nonwoven fabric, but may be aligned to the cross direction (CD) or oblique thereto. Note that the MD of the perforated nonwoven fabric constituting the top sheet 30 is, in most cases, aligned to the front-back direction LD.

The area of each aperture 14 and the area ratio of the apertures in the aperture arrayed region may suitably be decided, and the area may preferably be about 0.25 to 4.00 mm$^2$ and the area ratio may preferably be about 0.1 to 10%.

The pattern of the array of the apertures 14 may suitably be decided. For example, as shown in FIGS. 6(a), 6(c), and 6(d), it is preferred that the pattern of the array of the apertures 14 is a matrix wherein lines of apertures 14 aligned linearly in the front-back direction LD at predetermined intervals are repeated in the width direction WD at predetermined intervals. In this case, the apertures 14 may be arranged with the intervals 14y of the apertures 14 in the front-back direction LD being smaller than the intervals 14x of the apertures 14 in the width direction WD as shown in FIGS. 6(a) and 6(d), with the intervals 14y of the apertures 14 in the front-back direction LD being generally equal to the intervals 14x of the apertures 14 in the width direction WD as shown in FIG. 6(c), or with the intervals 14y of the apertures 14 in the front-back direction LD being larger than the intervals 14x of the apertures 14 in the width direction WD as shown in FIGS. 6(b) and 6(e). Further, as shown in FIGS. 6(a), 6(b), and 6(c), the lines 95 of apertures aligned linearly in the front-back direction LD at predetermined intervals may be arranged in the width direction WD at intervals and shifted with each other in the front-back direction LD. FIGS. 6(a) and 6(b) show examples of the arrangement wherein the apertures 14 in the adjacent lines 95 are staggered, i.e., so-called staggered pattern (hexagonal lattice pattern).

The intervals 14y of the apertures 14 in the front-back direction and the intervals 14x of the apertures 14 in the width direction may respectively be constant or varied, which may suitably be decided. For example, the intervals 14y of the apertures 14 in the front-back direction may be 0.9 to 8.0 mm, particularly 1.0 to 3.0 mm, whereas the intervals 14x of the apertures 14 in the width direction may be 2.0 to 10 mm, particularly 3.0 to 5.0 mm.

The pattern of the array of apertures 14 may also be such that groups 90 of apertures 14 aligned in the front-back direction LD with each group forming a single wavy line 91, 92 are arranged in the width direction WD at intervals in the same or different phases as shown in FIGS. 6(f) and 7. In the example of the pattern as shown in FIG. 7, the wave phases of the groups 90 of apertures 14 adjacent to each other in the width direction WD are opposite, so that the imaginary lines connecting the apertures 14 form a Moroccan pattern (ogee pattern). Further, as shown in FIG. 8, the pattern of the array of apertures 14 may also be such that groups 90 of apertures 14 aligned in the front-back direction LD at intervals with each group forming a chain-like pattern are arranged in the width direction WD at intervals. Here, "groups 90 of apertures 14 are arranged in the width direction WD at intervals" means that an imperforated zone 93 extending linearly unintermittently along the front-back direction LD is present between the groups 90 of apertures 14 adjacent to each other in the width direction WD.

The sectional shape of each aperture 14 is not particularly limited. For example, each aperture 14 may be a punched aperture of which periphery is formed with cut ends of fibers, or a non-punched aperture which hardly has cut ends of fibers on its periphery and is formed by inserting a pin into the space among fibers to expand (fiber density at the periphery is higher). The punched aperture may have a diameter tapered toward the middle of the thickness as shown in FIG. 9(d), or a diameter tapered toward one end in the thickness direction, not shown.

The non-punched aperture 14 has a diameter tapered from the pin-insertion side toward the opposite side of the aperture 14, which includes a diameter continuously tapered all over the thickness of a nonwoven fabric layer, and a diameter whose tapering is substantially ceased in the middle of the thickness. Such non-punched apertures 14 include those as shown in FIGS. 9(a) and 9(c) wherein fibers at the periphery of each aperture 14 on the side opposite to the pin-insertion side are extruded from the side opposite to the pin-insertion side to form a protrusion (burr) 14e, whereas a protrusion 14e is not formed on the pin-insertion side, and those as shown in FIG. 9(b) wherein fibers at the periphery of each aperture 14 on the side opposite to the pin-insertion side are extruded to the side opposite to the pin-insertion side to form a protrusion 14e, whereas fibers at the periphery of the aperture on the pin-insertion side are extruded to the pin-insertion side to form a protrusion 14e. The apertures 14 of the former type further include those as shown in FIG. 9(a) wherein the height 14h of the protrusion 14e is substantially even, and those as shown in FIG. 9(c) wherein the height 14i of the protrusion 14e is highest at two opposed locations whereas the level 14j of the protrusion 14e is lowest at two opposed locations orthogonal to the highest locations. It is preferred that the protrusion 14e continuously extends along the circumferential direction of the aperture to form a cylinder, but it is also conceivable that protrusions 14e of part or all of the apertures 14 are formed partially along the circumferential direction of the respective apertures 14. The heights 14h, 14i, 14j of the protrusion (nominal height determined under optical microscope without pressure) are preferably about 0.2 to 1.2 mm. Further, it is preferred that the maximum height 14i of the protrusion 14e is about 1.1 to 1.4 times the minimum height 14j of the protrusion 14e. The height of protrusion 14e may vary along the circumferential direction of the aperture 14.

When an aperture 14 longer in one direction, for example, as shown in FIGS. 6(a), 6(b), 6(d), is formed by pin insertion, the fibers at the periphery of the aperture 14 are displaced outwards or vertically to form a protrusion (burr) 14e having a height 14i at the longitudinally opposed locations of the aperture 14 higher than a height 14j at the opposed locations orthogonal to the longitudinal. The protrusion 14e around the aperture 14 may have a fiber density lower than the density around the protrusion, but preferably have a fiber density similar to or higher than the density around the protrusion.

In particular, when the perforated nonwoven fabric is continuous fiber nonwoven fabric having a fineness of 0.1 to 5.0 dtex (more preferably 1.0 to 3.0 dtex), a basis weight of 15 to 20 g/m² (more preferably 15 to 18 g/m²), and a thickness of 0.3 to 0.8 mm (more preferably 0.3 to 0.6 mm), and the apertures 14 are formed by pin insertion, the height of the protrusion 14e formed at the periphery of each aperture 14 is lower. More specifically, in the above-mentioned specific range of continuous fiber nonwoven fabric, the fibers are hard to be extruded in the thickness direction upon formation of the pin insertion apertures. This is because the fibers to which force is applied by the pin insertion are continuous and entangled all over the nonwoven fabric (continuous fiber), and displacement of a portion of the fibers to which force is applied by the pin insertion is withheld by the portions of the fibers continuous on the outer side thereof. Further, the above-mentioned specific range of continuous fiber nonwoven fabric basically has a moderately low fiber density, so that displacement of the fibers in the direction orthogonal to the thickness is relatively easy. As a result, when the above-mentioned specific range of continuous fiber nonwoven fabric is subjected to the pin insertion to form apertures 14 of the above-mentioned specific range of dimensions, during the pin insertion, the fibers around the pin are displaced toward the pin outlet side while the fibers are extruded radially outwardly of the direction of the pin insertion, which results in formation of the protrusions 14e, but with a lower height. Accordingly, at the periphery of each aperture 14, a higher-density area is formed which has a fiber density higher than that of the vicinity. With such a higher-density area, the contrast between the aperture and the periphery thereof is emphasized, so that the visibility of the apertures is advantageously improved.

(Intermediate Sheet)

For the purpose of immediately transferring the liquid permeated through the top sheet 30 to the absorber body, an intermediate sheet (also referred to as "second sheet") 40 may be provided, which has a higher liquid permeation rate compared to the top sheet 30. This intermediate sheet 40 is for immediately transferring the liquid to the absorber body to improve the absorption performance thereof, and to prevent the "back-flow" phenomenon of the absorbed liquid from the absorber body. The intermediate sheet 40 may be omitted.

The intermediate sheet 40 may be of a liquid-pervious sheet, such as nonwoven fabric. The intermediate sheet 40 may preferably be of air-through nonwoven fabric for its bulkiness. The air-through nonwoven fabric is preferably made of composite fibers of a core-clad structure, wherein the resin for the core may be polypropylene (PP), or preferably polyester (PET), which has a higher stiffness. The basis weight is preferably 17 to 80 g/m², more preferably 18 to 60 g/m². The fineness of the raw material fibers of the nonwoven fabric is preferably 2.0 to 10 dtex. For making nonwoven fabric bulky, it is also preferred to use eccentric fibers having off-centered cores, hollow fibers, or eccentric hollow fibers, entirely as the raw material fibers or partially mixed fibers.

In the illustrated embodiment, the intermediate sheet 40 is shorter than the absorber body 56 in width and is arranged in the center, but may be provided over the entire width. Further, the intermediate sheet 40 may be provided over the entire length of the diaper, or only in the middle portion in the front-back direction LD, including the excretion area, as in the illustrated embodiment.

(Liquid-Impervious Sheet)

The liquid-impervious sheet 11 is not particularly limited, and may preferably have moisture-permeability. As the liquid-impervious sheet 11, for example, a microporous sheet may preferably be used which is obtained by kneading an inorganic filler in a polyolefin-based resin, such as polyethylene or polypropylene, forming the resulting mixture into a sheet, and then uni- or biaxially drawing the sheet. Alternatively, the liquid-impervious sheet 11 may be formed of nonwoven fabric as a basic material, to which improved waterproof property is applied.

The liquid-impervious sheet 11 preferably extends over the same or wider extent than that of the absorber body 56 in the front-back direction LD and in the width direction WD but, when another liquid-shielding means is present, may not cover the ends or edges of the absorber body 56 in the front-back direction LD and in the width direction WD, as necessary.

(Exterior Nonwoven Sheet)

The exterior nonwoven sheet 12 covers the entire underside of the liquid-impervious sheet 11 to impart a fabric-like appearance to the product exterior. The exterior nonwoven sheet 12 preferably has a fiber basis weight of 10 to 50 g/m², in particular 15 to 30 g/m², which, however, is not limiting. The exterior nonwoven sheet 12 may be omitted, in which case the liquid-impervious sheet 11 may be extended to the side edges of the product.

(Standup Gather Part)

It is preferred to provide standup gather parts 60 which stand up toward the skin of the wearer on opposed sides in the width direction WD of the top face for blocking the bodily waste moving laterally on the top sheet 30 and thereby preventing so-called side leakage. Naturally, the standup gather parts 60 may be omitted.

The standup gather parts, when employed, may be of any structure without particular limitation, and may be any of various known structures. The standup gather parts 60 in the illustrated embodiment are each composed of a gathered sheet 62 continuous substantially in the width direction WD, and elongate gathering elastic members 63 fixed in their stretched state to the gathered sheet 62 along the front-back direction LD. The gathered sheet 62 may be of a water-repelling nonwoven fabric, whereas the gathering elastic members 63 may be of a rubber thread or the like. A plurality of the elastic members may be provided on each lateral side as shown in FIGS. 1 and 2, or only one elastic member may be provided on each lateral side.

The inner face of the gathered sheet 62 has a joining start edge positioned on a lateral side portion of the top sheet 30 in the width direction WD, and the portion outward in the width direction of this joining start edge is bonded to the inner face of the corresponding side flap SF, i.e., in the illustrate embodiment, a lateral side portion of the liquid-impervious sheet 11 and a lateral side portion of the exterior nonwoven sheet 12 located laterally outward thereof in the width direction, with a hot melt adhesive or the like.

Around each leg, each standup gather part 60 is fixed to the top sheet 30 on the center side of the joining start edge in the width direction at both end portions in the product front-back direction, while the remaining portion therebetween of the standup gather part 60 is a non-fixed free portion, which will be raised by the contracting force of the elastic members 63 to be brought into close contact with the body surface.

(End Flaps and Side Flaps)

The tape-type disposable diaper of the illustrated embodiment has a pair of end flaps EF exclusive of the absorber body 56, extending respectively on the front and back sides of the absorber body 56, and a pair of side flaps SF exclusive of the absorber body 56, extending respectively laterally beyond the opposed sides of the absorber body 56. The side flaps SF may be formed of the main body sheet (exterior nonwoven sheet 12 or the like) continuing from the portion containing the absorber body 56, or may be formed of another material and attached.

(Planar Gathers)

Each side flap SF is provided with side elastic members 64, which are of elongate elastic members, such as rubber threads, and are fixed in their stretched state in the front-back direction LD, to thereby form the round-leg portion of each side flap SF into planar gathers. The side elastic members 64 may be provided between the gathered sheet 62 and the liquid-impervious sheet 11 in the joined portion of the gathered sheet 62 in the outer vicinity in the width direction of the joining start edge as in the illustrated embodiment, or between the liquid-impervious sheet 11 and the exterior nonwoven sheet 12 in each side flap SF. A plurality of the side elastic members 64 may be provided on each lateral side as shown in the illustrated embodiment, or only one side elastic member 64 may be provided on each lateral side. Naturally, the side elastic members 64 (planar gathers) may be omitted.

The planar gathers are formed where the contracting force of the side elastic members 64 acts (in the illustrated embodiment, where the side elastic members 64 are shown). Thus, structures are conceivable, wherein the side elastic members 64 are present only in the area of the planar gathers, or wherein the side elastic members 64 are present on the front side, back side, or both of the planar gathers, but the contacting force of the side elastic members 64 acts only in the area of the planar gathers, while the contracting force is made not to act in the area other than the area of the planar gathers (substantially equivalent to absence of the elastic members) by finely cutting the side elastic members at one or a plurality of locations other than the area of the planar gathers, by not fixing the side elastic members 64 to the sheets between which the side elastic members 64 are interposed, or by both.

(Front Wings)

The present tape-type disposable diaper has front wings 80 extending on opposed sides of the product in the right-left direction at a position spaced forward of the middle of the product in the front-back direction. The front wings may be omitted (i.e., the product may be configured such that the width of the product is not varied from its narrowest portion to the front end).

The dimension of each front wing 80 in the width direction WD may suitably be decided and, for example, may be 5 to 20% (in particular 7 to 15%) the overall product length Y. The dimension of each front wing 80 in the width direction WD may be generally the same as the dimension of each back wing 81 to be discussed later in the width direction WD.

(Back Wings)

The present tape-type disposable diaper has back wings 81 extending on opposed sides of the product in the right-left direction at a position spaced backward of the middle of the product in the front-back direction.

The dimension of each back wing 81 in the width direction WD may suitably be decided and, for example, may be the same as the dimension of each front wing in the width direction WD, or smaller or larger than the dimension of the front wing in the width direction.

(Middle Section)

Each lateral edge of the product between the front wing 80 and the back wing 81 may have a generally linear portion passing the area of ±5 mm in the width direction on both sides of and in the direction orthogonal to a line at an acute angle of ±2 degrees or less with respect to the front-back direction LD. Each lateral edge of the product between the front wing 80 and the back wing 81 may extend in a wavy or arcuate manner (not shown), or in a linear manner as in the illustrated embodiment.

(Formation of Wings)

As in the illustrated embodiment, by cutting out each lateral side of the side flap SF in a concave shape, the overall concaved edge may be formed which extends from the lower edge of the front wing 80, via the lateral edge of the product between the front wing 80 and the back wing 81, to the lower edge of the back wing 81. In this case, the layered structure of the side flaps SF decides the layered structure of the front wings 80 and the back wings 81 and, in the illustrated embodiment, the front wings 80 and the back wings 81 are formed with gathered sheet 62 and the exterior nonwoven sheet 12. Though not shown, a front extension sheet may be provided extending laterally from each side flap SF to form all or edge-side part of each front wing 80 with the front extension sheet. Similarly, a back extension sheet may be provided extending laterally from each side flap SF to form all or edge-side part of each back wing 81 with the back extension sheet. The front extension sheet and the back extension sheet may be of various nonwoven fabric.

(Connecting Part)

Each back wing 81 is provided with a connecting part 13A to be detachably connected to the ventral section F when the product is worn. That is, in fitting the product, the opposed lateral side portions of the back wings 81 are brought onto the ventral side of the wearer, and the connecting parts 13A of the back wings 81 are connected to the exterior face of the ventral section F. The connecting part 13A may be a hook member (male part) of a mechanical fastener (hook and loop fastener), or a pressure-sensitive adhesive layer. The hook member has a number of engaging projections on its connecting surface, and the engaging projections may be in various known shapes, such as tick-shaped, J-shaped, mushroom-shaped, T-shaped, or double J-shaped (wherein J-shaped parts are joined back to back).

The connecting part 13A may directly be attached to the back wing 81, or a connecting tape 13 having the connecting part 13A may be attached to the back wing 81, as in the illustrated embodiment. The structure of the connecting tape 13 is not particularly limited and, in the illustrated embodiment, may have a tape attachment portion 13C fixed to the side flap SF, a tape body 13B protruding from the tape attachment portion 13C, and the connecting part 13A disposed in the middle of the tape body 13B in the width direction WD, and the portion beyond this connecting part 13A is a grip portion. The sheet material forming from the tape attachment portion 13C to the tape body 13B may be nonwoven fabric, plastic film, polyethylene-laminated nonwoven fabric, paper, or composites thereof.

A connecting site on the exterior face of the ventral section F to which the connecting parts 13A are to be connected, may suitably be decided, and only the body section located between the right and left front wings 80 may provide the connecting site, or the areas each extending from a lateral side portion of the body section toward the proximal side of the front wing 80 may provide the connecting site. To such connecting site, it is preferable that the connecting parts 13A may be easily connected. For example, when the connecting parts 13A are hook members (male parts) of mechanical fasteners (hook and loop fasteners), the connecting site on the exterior face of the ventral section F may be made with a loop member (female part) 20 of mechanical fasteners, or nonwoven fabric. As such a loop member 20, a plastic film stitched with a loop yarn is known, but in view of air permeability and flexibility, preferred is continuous fiber nonwoven fabric of which continuous fiber direction is its width direction WD (such as spunbonded nonwoven fabric generally having a fineness of 2.0 to 4.0 dtex, a basis weight of 20 to 50 g/m$^2$, and a thickness of 0.3 to 0.5 mm), provided with melt-bonded portions wherein fibers are melt-bonded with each other intermittently at least in the width direction WD. When a region of the exterior face of the ventral section F including the connecting site is formed with the exterior nonwoven sheet 12, the hook members may be connected to the exterior nonwoven sheet 12 without any other means added thereto. As in the illustrated embodiment, a loop member 20 may be adhered only to the connecting site on the exterior face of the ventral section F. Further, when the connecting parts 13A are in the form of pressure-sensitive adhesive layers, a plastic film having a smooth surface to be strongly adhered to the pressure-sensitive adhesive layers may be attached to the connecting site on the exterior face of the ventral section F.

(Fixing of Top Sheet)

The top sheet 30 is preferably bonded, via a hydrophobic hot melt adhesive 31, to an underside member arranged on the underside of the top sheet 30. Instead of or in addition to this, the top sheet 30 may be joined to an underside member arranged on the underside of the top sheet 30 by melt-bonding of at least one of the top sheet 30 and the underside member arranged on the underside of the top sheet 30. The area in which the top sheet 30 is fixed may, as long as the area extends at least over the entire aperture arrayed region, only be over the aperture arrayed region or extend beyond the aperture arrayed region to other areas (e.g., all over the top sheet 30). The underside member includes the intermediate sheet 40, the packing sheet 58, and the liquid-impervious sheet 11 in the illustrated embodiment, but is not limited thereto.

The hydrophobic hot melt adhesive 31 may be EVA-based, polyolefin-based, or polyester/polyamide-based adhesive or the like, and a pressure-sensitive rubber-based (elastomer-based) adhesive is particularly preferred.

The amount of the hydrophobic hot melt adhesive 31 to be applied may suitably be decided, and may usually be about 0.1 to 10 g/m$^2$. In particular, with the amount of the hydrophobic hot melt adhesive 31 being about 0.5 to 5 g/m$^2$, the hot melt adhesive 31 may preferably be kept from sticking out through the apertures 14, but interference with a hydrophilic lotion in bonding as will be discussed later is likely to occur, so that it is preferred to combine the application amount with designing of the application pattern of the hydrophilic lotion, or the like. The application pattern of the hydrophobic hot melt adhesive 31 may suitably be decided, and may preferably be a dense pattern with minute non-applied portions scattered all over (by spray application in spiral, Z, or wave shapes, or the like), or may be a continuous surface such as by slot application.

(Lotion-Bearing Zone)

The skin-touching region of the top sheet 30 has lotion-bearing zones 32 which bear a water-containing hydrophilic lotion, as shown in FIGS. 7, 10, and 11. With too small dimensions of each lotion-bearing zone, the friction-reducing effect is localized, which provides little significance in protection of the skin of a wearer, so that each lotion-bearing zone 32 preferably has a MD (the front-back direction LD in the illustrated embodiment) dimension 32 L of 30 mm or more and a CD (the width direction WD in the illustrated embodiment) dimension 32 W of 5 mm or more. The MD dimension 32 L of the lotion-bearing zone 32 is more preferably 50 mm or more, and particularly preferably 100 mm or more. The upper limit of the MD dimension 32 L of the lotion-bearing zone 32 is the overall product length Y, but may be shorter than this. The CD dimension 32 W of the lotion-bearing zone 32 is more preferably 10 mm or more. The upper limit of the CD dimension 32 W of the lotion-bearing zone 32 is the dimension in the width direction WD of the top sheet 30, but may be shorter than this.

The lotion-bearing zone 32 may be provided in one location with a relatively large area, or may be provided in a plurality of locations. The lotion-bearing zones 32 may preferably be provided in a striped pattern as in the illustrated embodiment, or in a horizontal-striped pattern. In such cases, the intervals 32X of the adjacent lotion-bearing zones 32 may suitably be decided, and may preferably be, for example, about 1.5 to 10 mm.

The nonwoven fabric for the top sheet 30 may preferably be discontinuous fiber nonwoven fabric having a fineness of 1 to 3 dtex (more preferably 1.5 to 2.5 dtex), a basis weight of 10 to 30 g/m$^2$ (more preferably 15 to 25 g/m$^2$), and a thickness of 0.4 to 1.4 mm (more preferably 0.5 to 1.0 mm). That is, with such discontinuous fiber nonwoven fabric, fineness of the fibers contributes to reduction of surface friction, which, in cooperation with the friction-reducing effect of the hydrophilic lotion, improves the overall friction-reducing effect. In addition, the fineness of the fibers also improves the hydrophilic lotion-retainability, which further improves the friction-reducing effect. More specifically, by the combination of the discontinuous fiber nonwoven fabric and the hydrophilic lotion, the lotion-bearing zones of the top sheet 30 preferably have an average coefficient of friction MIU of 0.2 to 0.4.

The surface moisture percentage of the lotion-bearing zones 32 is not particularly limited, and may preferably be 3 to 10%, particularly 4 to 8%, for moderately moistening and keeping the skin of a wearer from drying.

The hydrophilic lotion, as long as it contains water, may have any ingredient composition but water. For example, the components other than water of the hydrophilic lotion may be one or a plurality of members selected from glycerin, propylene glycol, dipropylene glycol, 1,3-butylene glycol, polyethylene glycol, sorbitol, xylitol, and sodium pyrrolidone carboxylate; and further sugars, such as trehalose, mucopolysaccharides (e.g., hyaluronic acid and derivatives thereof, chondroitin and derivatives thereof, heparin and derivatives thereof, or the like), elastin and derivatives thereof, collagen and derivatives thereof, NMF-related materials, lactic acid, urea, higher fatty acid octyldodecyl esters, seaweed extracts, *Bletilla striata* root extract, various amino acids and derivatives thereof, and the like. The hydrophilic lotion may further contain one or a plurality of additives selected from the group consisting of emulsifiers, phosphates, paraffin, and surfactants. The surfactants may preferably be ether-type nonionic surfactants or nonionic surfactants including EO/PO-type. For improved product storage stability, the hydrophilic lotion may contain a preservative but, as the hydrophilic lotion is to be transferred to the skin for moistening the same, it is more preferred that the hydrophilic lotion is free of preservatives.

A particularly preferred hydrophilic lotion contains 70 to 90 wt % glycerin and 10 to 30 wt % water. Such a hydrophilic lotion mainly composed of glycerin with a moderate amount of water, is preferred not only as a moisturizer when transferred to the skin, but also for its hardness to decay as the water is held in the glycerin as bound water (glycerin has an extremely high water retainability). That is, for using a water-containing hydrophilic lotion in this context, it is preferred to contain a large amount of glycerin, to ensure a sufficient surface moisture percentage (e.g., 3 to 10% as discussed above), and to keep a water activity value of the hydrophilic lotion low, for example, 0.8 or lower, more preferably 0.3 to 0.7, particularly preferably 0.3 to 0.5, so that, even in the absence of a preservative, development of microorganisms may be suppressed to provide improved shelf life, and the moisturizing effect upon transfer to the skin may be improved.

The content of the hydrophilic lotion in the lotion-bearing zones 32 may suitably be decided depending on the purpose. For example, with a hydrophilic lotion containing 70 to 90 wt % glycerin and 10 to 30 wt % water, the content per unit area of the lotion-bearing zones 32 is preferably 5 to 15 g/m$^2$. When a plurality of zones with different contents of the hydrophilic lotion is present as in the embodiment shown in FIG. 11, or when the applied amount of the hydrophilic lotion varies gradually, it is preferred that the content of the hydrophilic lotion all over the lotion-bearing zones is 2 to 20 g/m$^2$, the area of the lotion-bearing zones 32 having the content of the hydrophilic lotion of 5 to 15 g/m$^2$ is 20% or more, or both.

The discontinuous fiber nonwoven fabric is preferably formed of hydrophobic resin fibers for their low cost, which as they are have poor retainability of the water-containing hydrophilic lotion. Thus, the hydrophilic lotion preferably has a viscosity at 20° C. of 150 to 400 mPa·s. In this way, the hydrophilic lotion-retainability of the discontinuous fiber nonwoven fabric is preferably improved.

The discontinuous fiber nonwoven fabric is preferably formed of hydrophobic resin fibers for their low cost, which as they are have poor retainability of the water-containing hydrophilic lotion. Thus, it is preferred to use, as the top sheet, discontinuous fiber nonwoven fabric formed of hydrophilized fibers wherein hydrophobic resin fibers have been coated with a hydrophilizer. In this way, the hydrophilic lotion-retainability of the discontinuous fiber nonwoven fabric is preferably improved.

The hydrophilizer may preferably be, in consideration of safety for human body, safety in process, or the like factors, one or a mixture of nonionic activators obtained by addition of ethylene oxide to higher alcohols, higher fatty acids, alkylphenols, or the like, or anionic activators, such as alkyl phosphates (octyl or dodecyl) or alkyl sulfates. The amount to be applied may vary depending on the required performance, but may usually preferably be about 0.1 to 2.0 wt %, particularly about 0.2 to 1.0 wt % of the dry weight of the objective sheet.

<Efficacy Test>

Various samples of the top sheet as specified in Tables 1 to 3 were subjected to determination of various properties, including average coefficient of friction MIU, surface moisture percentage, and water activity value. Samples 1 to 10 were nonwoven fabric before fabrication into products, to which the hydrophilic lotion was or was not applied, and Samples 11 to 15 were top sheets removed from commercial products. Further, smoothness and moistness of each sample were perceived by stroking the top sheet surface in the longitudinal direction with the hand, and graded on three levels with respect to those of Sample 5 (⊙: excellent; Δ: better than Sample 5; ×: similar).

TABLE 1

| | | Sample number | | | | |
|---|---|---|---|---|---|---|
| | | 1 | 2 | 3 | 4 | 5 |
| Top sheet | Fineness (dtex) | 2.0(PE)/2.2(PET) | 2.0(PE)/2.2(PET) | 2.0(PE)/2.2(PET) | 2.0(PE)/2.2(PET) | 2.0(PE)/2.2(PET) |
| | Basis weight (g/m2) | 25 | 20 | 20 | 20 | 20 |
| | Thickness (mm) | 1.1 | 0.9 | 0.9 | 0.6 | 0.6 |
| | Material of fiber | PE/PET(mixed) | PE/PET(mixed) | PE/PET(mixed) | PE/PET(mixed) | PE/PET(mixed) |
| | Fiber joining | thermal bonding | thermal bonding | thermal bonding | thermal bonding | thermal bonding |
| Lotion-bearing zone | Arrangement | striped | striped | striped | striped | — |
| | MD dimension (mm) | 200 | 200 | 200 | 200 | — |
| | CD dimension (mm) | 5 | 5 | 5 | 5 | — |
| | Number (Interval 32 w) | 4(5) | 4(5) | 4(10) | 4(5) | — |
| | Basis weight (g/m2) | 8.5 | 8.5 | 8.5 | 8.5 | 0 |
| Lotion composition (wt %) | Glycerin | 76 | 76 | 76 | 76 | — |
| | Liquid paraffin | 2 | 2 | 2 | 2 | — |
| | Alkyl phosphate | 2 | 2 | 2 | 2 | — |
| | Water | 20 | 20 | 20 | 20 | — |
| Lotion viscosity (Pa · s) 20° c. | | 372 | 372 | 372 | 372 | — |
| Average coefficient of friction MIU | | 0.33 | 0.34 | 0.34 | 0.33 | 0.37 |
| Variation deviation of average coefficient of friction MMD | | 0.01 | 0.01 | 0.01 | 0.01 | 0.01 |
| Surface moisture percentage (%) | | 5.6 | 5.6 | 5.6 | 5.6 | 0.3 |
| Smoothness | | ⊙ | ⊙ | ⊙ | ⊙ | — |
| Moistness | | ⊙ | ⊙ | ⊙ | ⊙ | — |

TABLE 2

| | | Sample number | | | | |
|---|---|---|---|---|---|---|
| | | 6 | 7 | 8 | 9 | 10 |
| Top sheet | Fineness (dtex) | 2.0(PE)/2.2(PET) | 2.0(PE)/2.2(PET) | 2.0(PE)/2.2(PET) | 2.0(PE)/2.2(PET) | 2.2/3.3 |
| | Basis weight (g/m2) | 20 | 20 | 20 | 20 | 20 |

TABLE 2-continued

|  |  | Sample number | | | | |
|---|---|---|---|---|---|---|
|  |  | 6 | 7 | 8 | 9 | 10 |
| Lotion-bearing zone | Thickness (mm) | 0.6 | 0.6 | 0.6 | 0.6 | 0.6 |
|  | Material of fiber | PE/PET(mixed) | PE/PET(mixed) | PE/PET(mixed) | PE/PET(mixed) | PE/PET 2-layered |
|  | Fiber joining | thermal bonding | thermal bonding | thermal bonding | thermal bonding | thermal bonding |
|  | Arrangement | striped | striped | striped | striped | striped |
|  | MD dimension (mm) | 200 | 200 | 200 | 200 | 200 |
|  | CD dimension (mm) | 5 | 5 | 5 | 5 | 5 |
|  | Number (Interval 32 w) | 4(5) | 4(5) | 4(5) | 4(5) | 4(5) |
|  | Basis weight (g/m2) | 3.5 | 5.0 | 15.0 | 17.6 | 8.5 |
| Lotion composition (wt %) | Glycerin | 76 | 76 | 76 | 76 | 76 |
|  | Liquid paraffin | 2 | 2 | 2 | 2 | 2 |
|  | Alkyl phosphate | 2 | 2 | 2 | 2 | 2 |
|  | Water | 20 | 20 | 20 | 20 | 20 |
| Lotion viscosity (Pa · s) 20° c. |  | 372 | 372 | 372 | 372 | 372 |
| Average coefficient of friction MIU |  | 0.41 | 0.40 | 0.30 | 0.30 | 0.51 |
| Variation deviation of average coefficient of friction MMD |  | 0.01 | 0.01 | 0.01 | 0.01 | 0.01 |
| Surface moisture percentage (%) |  | 3.0 | 4.2 | 8.0 | 8.9 | 3.0 |
| Smoothness |  | ○ | ○ | ◎ | ◎ | Δ |
| Moistness |  | ○ | ○ | ◎ | ◎ | Δ |

TABLE 3

|  |  | Sample number | | | | |
|---|---|---|---|---|---|---|
|  |  | 11 | 12 | 13 | 14 | 15 |
| Top sheet | Fineness (dtex) | Company A Commercial diaper 1 | Company B Commercial diaper 1 | Company A Commercial diaper 2 | Company B Commercial diaper 2 | Company C Commercial diaper |
|  | Basis weight (g/m2) |  |  |  |  |  |
|  | Thickness (mm) |  |  |  |  |  |
|  | Material of fiber |  |  |  |  |  |
|  | Fiber joining |  |  |  |  |  |
| Lotion-bearing zone | Arrangement | — | — | — | — | — |
|  | MD dimension (mm) | — | — | — | — | — |
|  | CD dimension (mm) | — | — | — | — | — |
|  | Number (Interval 32 w) | — | — | — | — | — |
|  | Basis weight (g/m2) | — | — | — | — | — |
| Lotion composition (wt %) | Glycerin | — | — | — | — | — |
|  | Liquid paraffin | — | — | — | — | — |
|  | Alkyl phosphate | — | — | — | — | — |
|  | Water | — | — | — | — | — |
| Lotion viscosity (Pa · s) 20° c. |  | — | — | — | — | — |
| Average coefficient of friction MIU |  | 0.65 | 0.62 | 0.48 | 0.69 | 0.58 |
| Variation deviation of average coefficient of friction MMD |  | 0.01 | 0.01 | 0.01 | 0.01 | 0.01 |
| Surface moisture percentage (%) |  | 0.3 | 0.1 | 0.2 | 0.3 | 0.3 |
| Smoothness |  | X | X | Δ | X | X |
| Moistness |  | X | X | X | X | X |

As may be seen from Tables 1 to 3, it was revealed that the surface of the top sheets of Samples 1 to 4 and 6 to 9, in particular Samples 1 to 4, 8, and 9, were perceived as being very smooth and moist. Compared to these, Samples 10 to 15 were inferior in smoothness and moistness. Sample 9 was moist but provided sticky feel.

<Explanation of Terms in the Specification>

The following terms appearing in the present specification shall have the following means unless otherwise specified herein.

The "front-back direction" refers to the direction shown by the reference sign LD (longitudinal direction) in the figures, whereas the "width direction" refers to the direction shown by the reference sign WD (right-left direction) in the figures, and the front-back direction and the width direction are orthogonal to each other.

The "machine direction (MD)" and "cross direction (CD)" refer to the flow direction (MD) and the lateral direction orthogonal thereto (CD) in the production facilities, respectively, and either one of these is aligned to the front-back direction while the other is aligned to the width direction, depending on the parts of the product. The MD of nonwoven fabric is the direction of fiber orientation in the nonwoven fabric. The fiber orientation refers to the direction along which the fibers of the nonwoven fabric are aligned, and may be identified, for example, by a measurement method pursuant to the fiber orientation testing method using zero-span tensile strength prescribed in TAPPI Standard Method T481, or by a simplified measurement method for determining the fiber orientation by the ratio of tensile strengths in the front-back direction and in the width direction.

The "top side" refers to the side, when the article is worn, closer to the skin of the wearer, whereas the "underside" refers to the side, when the article is worn, away from the skin of the wearer.

The "top face" refers to the face, when the article is worn, closer to the skin of the wearer, whereas the "under face" refers to the face, when the article is worn, away from the skin of the wearer.

The "area ratio" refers to the ratio of the objective area per unit area, and is calculated by dividing the sum of the areas of objective portions (e.g., apertures) in an objective region (e.g., cover nonwoven sheet) by the area of that objective region, and is represented in percentage. In a configuration where a number of objective portions are provided at intervals, the area ratio is preferably determined with the objective region being set to a size containing 10 or more objective portions. For example, the area ratio of the apertures may be determined in the following procedure, using, for example, VHX-1000 (trade name) manufactured by KEYENCE under the measurement conditions in ×200 magnification.

(1) Place a specimen under a ×20 magnification lens, and adjust the focus. Position the nonwoven fabric so that 4×6 apertures are in the field.
(2) Specify the brightness of the pore portions, and measure the area of the holes.
(3) Click the color extraction in "Area Measurement" under "Measurement and Comment". Click the pore portions.
(4) Click "collective Measurement", check "Display measurement result window", and store in CSV data.

The "stretch rate" refers to a value with respect to the natural length being 100%. For example, a 200% stretch rate is synonymous with stretch in two folds.

The "gel strength" is determined as follows. To 49.0 g of artificial urine (a mixture of 2 wt % urea, 0.8 wt % sodium chloride, 0.03 wt % calcium chloride dihydrate, 0.08 wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curd-meter-MAX ME-500 manufactured by I. techno Engineering).

The "basis weight" is determined as follows. A specimen or test piece is preliminarily dried, left in a laboratory or in apparatus under the standard conditions (23±1° C. temperature and 50±2% relative humidity in the testing location) until constant mass is attained. The preliminary drying refers to attaining constant mass from a specimen or test piece in the environment at a temperature of 100° C. No preliminary drying may be performed on fibers with an official regain of 0.0%. From the test piece of the constant mass, a specimen of 100 mm×100 mm size is cut out using a sampling template (100 mm×100 mm). The weight of the specimen is measured and multiplied by 100 times to calculate the weight per 1 $m^2$, which is taken as the basis weight.

The "thickness" is automatically measured using an automatic thickness meter (KES-G5 handy compression tester program) under a load of 0.098 $N/cm^2$ with the compression area of 2 $cm^2$. The thickness of perforated nonwoven fabric is measured at a position other than the apertures and the protrusions therearound.

The water absorption is determined in accordance with JIS K7223—1996 "Testing method for water absorption capacity of super absorbent polymers".

The water absorption rate is defined as the "time spent until the end point is reached" in carrying out JIS K7224—1996 "Testing method for water absorption rate of super absorbent polymers" using 2 g of superabsorbent polymer and 50 g of saline.

The "spread state" refers to the state in which an article is spread flatly without contraction or slack.

The size of each part refers to the size not in the natural length state but in the spread state, unless otherwise specified.

The "melt viscosity" is determined at a prescribed temperature using a Brookfield B-type viscometer (spindle No. 027) in accordance with JIS Z 8803.

The "maximum dimension" of an aperture refers to the longer of the MD dimension and the CD dimension.

The "average coefficient of friction MIU" and the "variation deviation of average coefficient of friction MMD" is determined using a friction tester KES-SE manufactured by KATO TECH CO., LTD. (10 mm square silicon sensor, 50 g load), and refers to the value measured for the sensor moving distance of 20 mm. The sensor moving direction (direction of friction) is the MD of the top sheet. When a product is to be subjected to the measurement, members constituting the product except for the top sheet are removed or cut out to the extent that the friction test on the top sheet surface would not be affected (as such, members, for example, melt-bonded to the top sheet will not be removed), and the test is conducted on the top sheet in its spread state.

In addition, when the CD dimension of a lotion-bearing zone on the top sheet is less than the sensor dimension (10 mm), the top sheet 30 is cut along the lateral edges of the lotion-bearing zone 32 as shown in FIG. 12(*a*) to obtain a specimen 300 solely of the lotion-bearing zone 32 (narrower in width than the sensor 100), and this specimen is subjected to measurement with the center of the sensor 100 being aligned to the center of the specimen 300 in the CD as shown in FIG. 12(*b*). In every measurement, the hydrophilic lotion remaining on the surface of the sensor 100 is thoroughly wiped off before next measurement.

The lotion-bearing zones, if cannot be identified visually, may be identified through appropriate measures. For example, a necessary number of specimens (for measurement and for positional identification) are provided, which have the lotion-bearing zones 32 at the same positions, the lotion-bearing zones 32 on the top sheet 30 of a specimen for positional identification are colored with an appropriate coloring agent in a color different from that of the surroundings, the colored areas are identified using a ruler or other proper image measurement device, and then the measurement is made on a specimen for measurement at the same positions as those of the colored areas identified in the specimen for positional identification, which positions are regarded as the lotion-bearing zones 32. For coloring the lotion-bearing zones 32, a water leak testing agent MORAY-MILLE W manufactured by TASETO CO., LTD. may preferably be used. The lotion-bearing zones 32 may be identified by this process also for measurement of the MD dimension 32 L and CD dimension 32 W of a lotion-bearing zone 32, or for determination of surface moisture percentage to be discussed below.

The "surface moisture percentage" is an average calculated from the values measured at three arbitrary positions in the lotion-bearing zones 32 using a moisture checker MY-808S manufactured by SCALAR CORPORATION. Note that in every measurement, the hydrophilic lotion remaining on the measuring surface of the moisture checker is thoroughly wiped off before next measurement.

The "water activity value" may be determined using an electric resistance-type water activity meter, such as EZ-100 ST (electric resistance type) manufactured by FREUND CORPORATION. Before measurement, calibration is performed with a saturated solution. Measurement may be made according to an electric resistance-type test based on Standard Methods of Analysis in Food Safety Regulation. Specifically, a sample is taken in a volume of 3% or more the inner capacity of the detector of the water activity meter, placed on an aluminum foil dish or an open flat plate, immediately introduced into and sealed in the detector, and subjected to the conditions of 25±2° C. The values are read every 10 minutes and, when fluctuation of the value is no longer observed, the water vapor pressure in the detector is regarded as in equilibrium, and the value at that point is taken as the measured value of that sample. Each sample is measured three times, and the average of the three measured values is taken as the water activity value.

The "viscosity" is determined at a prescribed temperature using a Brookfield B-type viscometer (spindle No. 027) in accordance with JIS Z 8803/

A test or measurement shall be, in the absence of description about environmental conditions, performed in a laboratory or in apparatus under the standard conditions (23±1° C. temperature and 50±2% relative humidity in the testing location).

INDUSTRIAL APPLICABILITY

The present invention is applicable not only to underpants-type disposable diapers or tape-type disposable diapers, but also to general disposable wearable articles, such as pad-type disposable diapers, disposable swim wears, diaper covers, or sanitary napkins.

DESCRIPTION OF REFERENCE SIGNS

11: liquid-impermeable sheet
12: exterior nonwoven sheet
14: aperture
14e: protrusion
20: loop member
30: top sheet
40: intermediate sheet
50: absorbent element
56: absorber body
58: packing sheet
60: standup gather part
62: gathered sheet
LD: front-back direction
WD: width direction
90: group
93: imperforated zone
31: hydrophobic hot melt adhesive
32: lotion-bearing zone
94: unit arrayed area

The invention claimed is:

1. A disposable wearable article comprising a top sheet having a skin-touching region that is brought into contact with skin of a wearer,
   wherein the top sheet is made from discontinuous fiber nonwoven fabric having a fineness of 1 to 3 dtex, a basis weight of 10 to 30 g/m$^2$, and a thickness of 0.4 to 1.4 mm,
   wherein the discontinuous fiber nonwoven fabric is nonwoven fabric formed of hydrophilized fibers in which hydrophobic resin fibers have been coated with a hydrophilizer,
   wherein the skin-touching region has a lotion-bearing zone in which a water-containing hydrophilic lotion is applied,
   wherein the hydrophilic lotion contains 70 to 90 wt % glycerin and 10 to 30 wt % water,
   wherein the hydrophilic lotion has a viscosity at a temperature of 20° C. of 150 to 400 mPa·s,
   wherein the lotion-bearing zone has a machine direction dimension of 30 mm or larger and a cross direction dimension of 5 mm or larger, and
   wherein an average coefficient of friction MIU of the lotion-bearing zone is 0.2 to 0.4.

2. The disposable wearable article according to claim 1, wherein the lotion-bearing zone has a surface moisture percentage of 3 to 10%.

3. The disposable wearable article according to claim 2, wherein a content of the hydrophilic lotion per unit area of the lotion-bearing zone is 5 to 15 g/m$^2$.

* * * * *